(12) United States Patent
Sakayanagi

(10) Patent No.: US 7,320,746 B2
(45) Date of Patent: Jan. 22, 2008

(54) CONCENTRATION DETECTOR

(75) Inventor: Yoshihiro Sakayanagi, Susono (JP)

(73) Assignee: Toyota Jidosha Kabushiki Kaisha, Toyota (JP)

( * ) Notice: Subject to any disclaimer, the term of this patent is extended or adjusted under 35 U.S.C. 154(b) by 478 days.

(21) Appl. No.: 10/899,122

(22) Filed: Jul. 27, 2004

(65) Prior Publication Data

US 2005/0040041 A1    Feb. 24, 2005

(30) Foreign Application Priority Data

Aug. 20, 2003    (JP)    ............... 2003-208060

(51) Int. Cl.
*G01N 27/41*    (2006.01)
(52) U.S. Cl. .............. 204/425; 204/426; 205/781; 73/23.31
(58) Field of Classification Search ............... 204/425, 204/426, 427; 205/781, 784; 73/23.31
See application file for complete search history.

(56) References Cited

U.S. PATENT DOCUMENTS 6,045,673 A * 4/2000 Kato et al. .............. 204/425
6,071,393 A * 6/2000 Oshima et al. .............. 204/425
2002/0179594 A1* 12/2002 Hada et al. .............. 219/494

FOREIGN PATENT DOCUMENTS

| EP | 1 202 048 A2 | 5/2002 |
|---|---|---|
| JP | A 8-178896 | 7/1996 |
| JP | A 9-113482 | 5/1997 |
| JP | A-2000-137018 | 5/2000 |
| JP | A 2001-141696 | 5/2001 |
| JP | A 2001-330586 | 11/2001 |
| JP | A 2002-202285 | 7/2002 |
| JP | A-2003-294696 | 10/2003 |
| JP | A-2004-198351 | 7/2004 |

\* cited by examiner

*Primary Examiner*—Kaj K. Olsen
(74) *Attorney, Agent, or Firm*—Oliff & Berridge, PLC

(57) ABSTRACT

A concentration detector for detecting the concentration of a particular component in a gas based upon the amount of oxygen formed by the decomposition of the particular component, comprising oxygen-forming means for forming oxygen by decomposing the above particular component, oxygen-discharging means for discharging oxygen from the gas before oxygen is formed by the oxygen-forming means, and oxygen-discharging capability-increasing means for increasing the oxygen-discharging capability of the oxygen-discharging means when the rate of increase of the oxygen concentration in the gas is greater than a predetermined rate before oxygen is formed by the oxygen-forming means.

5 Claims, 4 Drawing Sheets

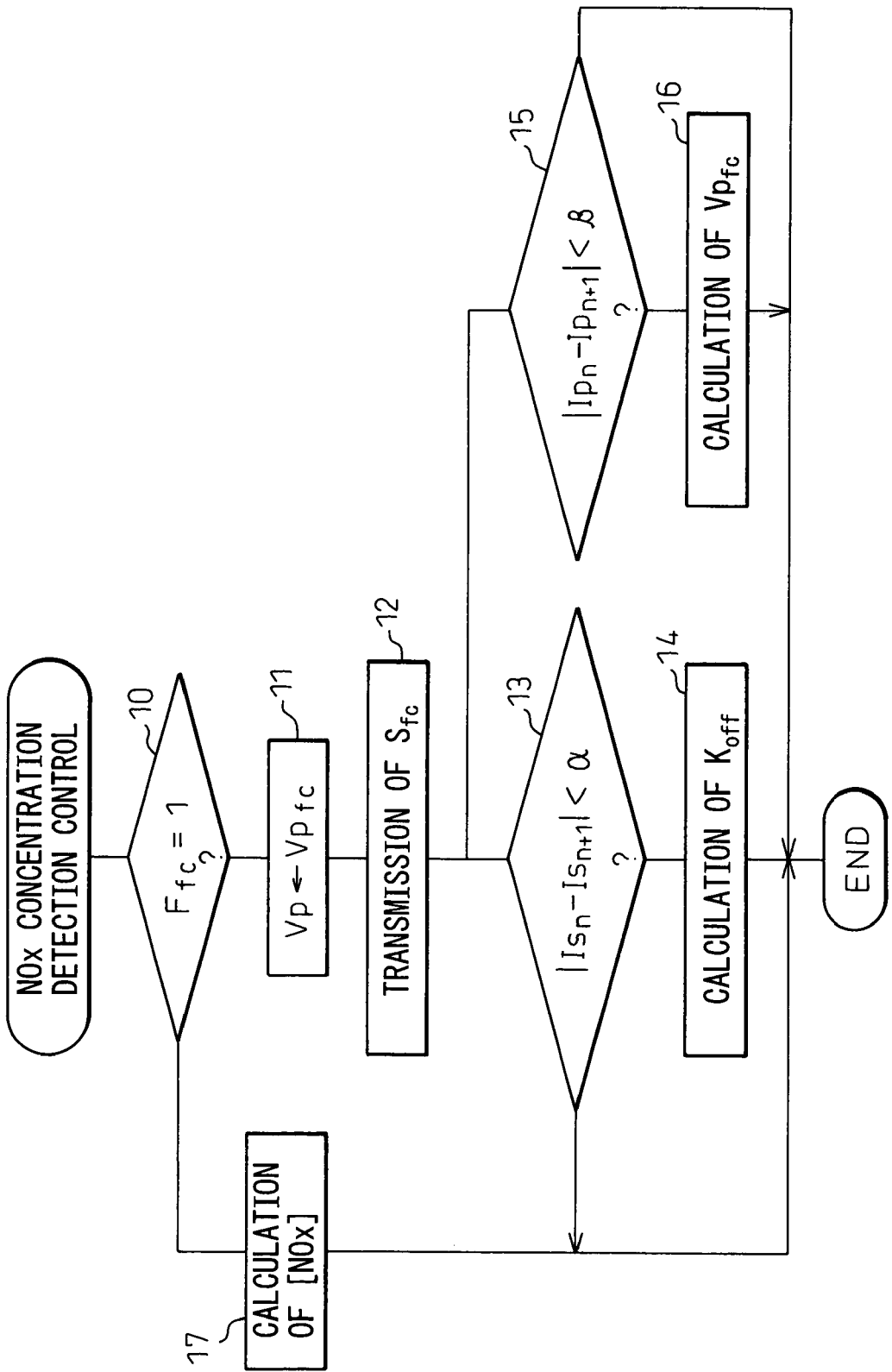

CONCENTRATION DETECTOR

BACKGROUND OF THE INVENTION

1. Field of the Invention

The present invention relates to a concentration detector. More particularly, the invention relates to a concentration detector for detecting the concentration of NOx (nitrogen oxides) in the exhaust gas emitted from an internal combustion engine.

2. Description of the Related Art

Japanese Unexamined Patent Publication (Kokai) No. 8-178896 discloses an air-fuel ratio detector for detecting an oxygen concentration in the exhaust gas emitted from an internal combustion engine and for calculating (detecting) the air-fuel ratio from the oxygen concentration that is detected. The air-fuel ratio detector of the above Japanese Unexamined Patent Publication (Kokai) No. 8-178896 is provided with a pair of electrodes (which, in Japanese Unexamined Patent Publication (Kokai) No. 8-178896, are called pump electrodes and are designated at 12 and 13) for pumping out oxygen from the exhaust gas. When a voltage is applied across the electrodes in the above air-fuel ratio detector, oxygen in the exhaust gas is pumped out. Here, the voltage applied across the electrodes is controlled depending upon the oxygen concentration in the exhaust gas.

In the air-fuel ratio detector disclosed in Japanese Unexamined Patent Publication (Kokai) No. 8-178896 as described above, a voltage corresponding to the oxygen concentration in the exhaust gas is applied across the electrodes. According to Japanese Unexamined Patent Publication (Kokai) No. 8-178896, however, when the internal combustion engine is in a normal operating condition (i.e., in an operating condition excluding an operating condition where no fuel is fed to the internal combustion engine, hereinafter referred to as a "normal engine operating condition"), the voltage applied across the above electrodes is maintained smaller than a predetermined voltage. Therefore, a judgement is rendered that the air-fuel ratio detector is abnormal if the voltage applied across the electrodes is greater than the predetermined value while the engine is normally operating. When no fuel is supplied to the internal combustion engine (hereinafter referred to as a "fuel cut"), however, the oxygen concentration in the exhaust gas increases and becomes nearly equal to the oxygen concentration in the atmosphere. Therefore, the voltage applied across the electrodes becomes greater than the predetermined value even though the air-fuel ratio detector is not abnormal. According to the method of judging an abnormal condition in the air-fuel ratio detector disclosed in the above Japanese Unexamined Patent Publication (Kokai) No. 8-178896, in this case, it is so judged that the air-fuel ratio detector is abnormal. However, it is highly probable that the result of this judgement is incorrect. According to Japanese Unexamined Patent Publication (Kokai) No. 8-178896, therefore, the abnormal condition of the air-fuel ratio detector is not judged when the fuel is being cut.

Namely, according to Japanese Unexamined Patent Publication (Kokai) No. 8-178896, when the air-fuel ratio detector is normally functioning, an abnormal condition in the air-fuel ratio detector is judged based on a prerequisite that the oxygen concentration in the exhaust gas is smaller than a predetermined concentration during the normal operation of the engine, but the abnormal condition in the air-fuel ratio detector is not judged when the fuel is cut because the oxygen concentration in the exhaust gas becomes greater than a predetermined concentration. When the fuel is cut as described above, the oxygen concentration in the exhaust gas increases rapidly. In order for the air-fuel ratio detector to work normally, therefore, the air-fuel ratio detector must be furnished with a particular control operation.

There has been known a NOx concentration detector for detecting the concentration of NOx (nitrogen oxide) in the exhaust gas. As the NOx concentration detector of this kind, there has been known the one according to which oxygen is removed from the exhaust gas and, then, NOx in the exhaust gas is decomposed to newly form oxygen, and the NOx concentration is estimated from the concentration of oxygen that is newly formed. Even in this NOx concentration detector, the function is affected by the oxygen concentration in the exhaust gas. To maintain a normal function, therefore, the NOx concentration detector must be furnished with some special control means, when the fuel is cut, as described in Japanese Unexamined Patent Publication (Kokai) No. 8-178896.

This applies not only to the NOx concentration detector for detecting the NOx concentration in the exhaust gas but also to general concentration detectors for detecting the concentrations of particular components in the gas and of which the functions are affected by the oxygen concentration in the gas.

It is therefore an object of the present invention to provide a concentration detector for detecting the concentration of a particular component in the gas and maintaining a normal function even when the fuel is being cut.

SUMMARY OF THE INVENTION

In order to solve the above problem according to a first invention, there is provided a concentration detector for detecting the concentration of a particular component in a gas, which component forms oxygen by decomposition, based upon the amount of oxygen formed by the decomposition of the particular component, comprising oxygen-forming means for forming oxygen by decomposing the above particular component, oxygen-discharging means for discharging oxygen from the gas before oxygen is formed by the oxygen-forming means, and oxygen-discharging capability-increasing means for increasing the oxygen-discharging capability of the oxygen-discharging means when the rate of increase of the oxygen concentration in the gas is greater than a predetermined rate before oxygen is formed by the oxygen forming-means. Here, the oxygen-forming means and the oxygen-discharging means correspond to a sensor cell and a pump cell (or a combination of the pump cell and a monitor cell), respectively, in the embodiment of the invention described later. In the embodiment of the invention described later, further, the particular component corresponds to NOx, ammonia or SOx.

In a second invention, as set forth in the first invention, the oxygen-discharging capability of the oxygen-discharging means varies depending upon a voltage applied to the oxygen-discharging means, the voltage applied to the oxygen-discharging means is controlled depending upon the oxygen concentration in the gas after the oxygen-discharging capability of the oxygen-discharging means has been increased by the oxygen-discharging capability-increasing means, and a degree of increasing the oxygen-discharging capability of the oxygen-discharging means by the oxygen-discharging capability-increasing means is determined based on the voltage applied to the oxygen-discharging means after the oxygen-discharging capability of the oxygen-discharging means is increased by the oxygen-discharging capability-increasing means.

A third invention, as set forth in the first invention, further comprises concentration calculation means for calculating the concentration of a particular component in the gas based on a current generated depending upon the oxygen concentration in the gas after oxygen is formed by the oxygen-forming means, and means for calculating a coefficient for correcting a calculation error in the concentration calculation means based on a current generated depending upon the oxygen concentration in the gas when the rate of increase of the oxygen concentration in the gas becomes greater than the predetermined rate before oxygen is formed by the oxygen-forming means.

In a fourth invention, as set forth in the first invention, the concentration detector is disposed in the exhaust gas passage which is for passing the exhaust gas emitted from the internal combustion engine, the gas is the exhaust gas emitted from the internal combustion engine, and when no fuel is supplied to the internal combustion engine, the rate of increase of the oxygen concentration in the gas becomes greater than the predetermined rate before oxygen is formed by the oxygen-forming means.

In a fifth invention, as set forth in the first invention, the particular component is one of nitrogen oxide and ammonia.

BRIEF DESCRIPTION OF THE DRAWINGS

The present invention may be more fully understood from the description of the preferred embodiments of the invention set forth below together with the accompanying drawings, in which:

FIG. 4 is a flowchart illustrating the NOx concentration detection (calculation) control according to the present invention.

DESCRIPTION OF THE PREFERRED EMBODIMENTS

Figure 1:
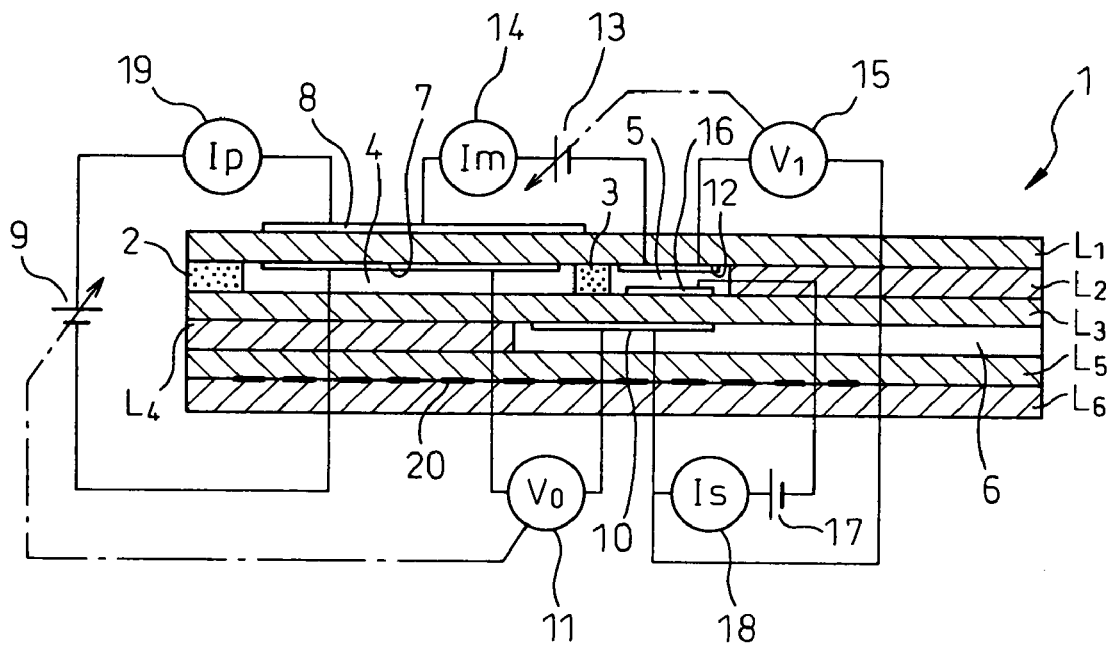
FIG. 1 is a view illustrating a sensor portion of a NOx sensor according to an embodiment of the present invention.

An embodiment of the invention will now be described with reference to the drawings. FIG. 1 illustrates the structure of a sensor portion of the NOx sensor for detecting the concentration of nitrogen oxide (NOx) in the gas. The following description deals with the NOx sensor of the embodiment which is mounted on an exhaust pipe of an internal combustion engine for detecting the NOx concentration in the exhaust gas emitted from the combustion chamber of the internal combustion engine.

Referring to FIG. 1, a sensor portion 1 of the NOx sensor comprises six electrolytic layers of an oxygen ion conducting solid electrolyte (e.g., zirconium oxide) laminated one upon the other. Hereinafter, these six solid electrolytic layers are referred to, from the upper side, as first layer $L_1$, second Layer $L_2$, third layer $L_3$, fourth layer $L_4$, fifth layer $L_5$ and sixth layer $L_6$.

Between the first layer $L_1$ and the third layer $L_3$, there are arranged a first diffusion rate-determining member 2 and a second diffusion rate-determining member 3 made of, for example, a porous material (or fine pores have been formed therein). A first chamber 4 is formed between the diffusion rate-determining members 2 and 3. A second chamber 5 is formed between the second diffusion rate-determining member 2 and the second layer $L_2$. Further, an atmospheric chamber 6 communicated with the atmosphere is formed between the third layer $L_3$ and the fifth layer $L_5$. The outer side surface of the first diffusion rate-determining member 2 comes in contact with the exhaust gas. Therefore, the exhaust gas flows into the first chamber 4 through the first diffusion rate-determining member 2, and the interior of the first chamber 4 is filled with the exhaust gas.

A first cathode-side pump electrode 7 is formed on the inner peripheral surface of the first layer $L_1$ facing the first chamber 4. A first anode-side pump electrode 8 is formed on the outer peripheral surface of the first layer $L_1$. A voltage is applied across these first pump electrodes 7 and 8 from a first pump voltage source 9. When the voltage is applied across the first pump electrodes 7 and 8, oxygen contained in the exhaust gas in the first chamber 4 turns into oxygen ions upon coming in contact with the first cathode-side pump electrode 7. The oxygen ions flow toward the first anode-side pump electrode 8 through the first layer $L_1$. Therefore, oxygen contained in the exhaust gas in the first chamber 4 is pumped out through the first layer $L_1$. Here, the amount of oxygen pumped out increases with an increase in the voltage of the first pump voltage source 9.

A reference electrode 10 is formed on the wall surface of the third layer $L_3$ facing the atmospheric chamber 6. Here, in the oxygen ion conducting solid electrolyte, if there is a difference in the oxygen concentration on both sides of the solid electrolytic layer, the oxygen ions migrate through the solid electrolytic layer from the side of a high oxygen concentration toward the side of a low oxygen concentration. In the example illustrated in FIG. 1, the oxygen concentration in the atmospheric chamber 6 is higher than the oxygen concentration in the first chamber 4. Upon coming in contact with the reference electrode 10, therefore, oxygen in the atmospheric chamber 6 receives electric charge and turns into oxygen ions. The oxygen ions migrate through the third layer $L_3$, second layer $L_2$ and first layer $L_1$ and emit electric charges to the first cathode-side pump electrode 7. As a result, a voltage $V_0$ designated at 11 is generated across the reference electrode 10 and the first cathode-side pump electrode 7. This voltage $V_0$ varies in proportion to the difference between the oxygen concentration in the atmospheric chamber 6 and the oxygen concentration in the first chamber 4.

In the example illustrated in FIG. 1, further, the voltage of the first pump voltage source 9 is so controlled by feedback that the voltage $V_0$ is brought into agreement with a voltage that is generated when the oxygen concentration in the first chamber 4 is 1 p.p.m. (this value is merely an example and may lie between, for example, several p.p.m. and several tens of p.p.m.). Namely, oxygen in the first chamber 4 is pumped out through the first layer $L_1$ such that the oxygen concentration in the first chamber 4 is 1 p.p.m. Thus, the oxygen concentration in the first chamber 4 is maintained at 1 p.p.m.

The first cathode-side pump electrode 7 is made of a material (e.g., an alloy of gold (Au) and platinum (Pt)) that hardly reduces NOx. Therefore, NOx contained in the exhaust gas is hardly reduced in the first chamber 4. Namely, NOx flows into the second chamber 5 passing through the second diffusion rate-determining member 3.

A second cathode-side pump electrode 12 is formed on the inner peripheral surface of the first layer $L_1$ facing the second chamber 5. A voltage is applied across the second cathode-side pump electrode 12 and the first anode-side pump electrode 8 from a second pump voltage source 13. When the voltage is applied across the pump electrodes 12 and 8, oxygen contained in the exhaust gas in the second chamber 5 turns into oxygen ions upon coming in contact with the second cathode-side pump electrode 12. The oxygen ions flow toward the first anode-side pump electrode 8 through the first layer $L_1$. Therefore, oxygen contained in the exhaust gas in the second chamber 5 is pumped out through the first layer $L_1$. Here, the amount of oxygen pumped out increases with an increase in the voltage of the second pump voltage source 13. Here, further, an electric current Im designated at 14, which is proportional to the amount of oxygen ions, flows between the second cathode-side pump electrode 12 and the first anode-side pump electrode 8.

In the oxygen ion conducting solid electrolyte, as described above, if there is a difference in the oxygen concentration on both sides of the solid electrolytic layer, the oxygen ions migrate through the solid electrolytic layer from the side of a high oxygen concentration toward the side of a low oxygen concentration. In the example illustrated in FIG. 1, the oxygen concentration in the atmospheric chamber 6 is higher than the oxygen concentration in the second chamber 5. Upon coming in contact with the reference electrode 10, therefore, oxygen in the atmospheric chamber 6 receives electric charges and turns into oxygen ions. The oxygen ions migrate through the third layer $L_3$, second layer $L_2$ and first layer $L_1$ and emit electric charges to the second cathode-side pump electrode 12. As a result, a voltage $V_1$ designated at 15 is generated across the reference electrode 10 and the second cathode-side pump electrode 12. This voltage $V_1$ varies in proportion to the difference between the oxygen concentration in the atmospheric chamber 6 and the oxygen concentration in the second chamber 5.

In the example illustrated in FIG. 1, the voltage of the second pump voltage source 13 is so controlled by feedback that the voltage $V_1$ is brought into agreement with a voltage that is generated when the oxygen concentration in the second chamber 5 is 0.01 p.p.m. (this value is merely an example and may assume any other value). Namely, oxygen in the second chamber 5 is pumped out through the first layer $L_1$ such that the oxygen concentration in the second chamber 5 is 0.01 p.p.m. Thus, the oxygen concentration in the second chamber 5 is maintained at 0.01 p.p.m.

The second cathode-side pump electrode 12 is made of a material (e.g., an alloy of gold (Au) and platinum (Pt)) that hardly reduces NOx. Therefore, NOx contained in the exhaust gas is hardly reduced even when it comes in contact with the second cathode-side pump electrode 12.

Further, a cathode-side pump electrode 16 for detecting NOx is formed on the wall surface of the third layer $L_3$ facing the second chamber 5. The cathode-side pump electrode 16 is made of a material (e.g., rhodium (Rh) or platinum (Pt)) that strongly reduces NOx. Therefore, NOx (in practice, NO occupying a major proportion) in the second chamber 5 is decomposed into $N_2$ and $O_2$ on the cathode-side pump electrode 16. Referring to FIG. 1, a predetermined voltage 17 is applied across the cathode-side pump electrode 16 and the reference electrode 10. Therefore, oxygen that is formed by decomposition on the cathode-side pump electrode 16 migrates in the form of oxygen ions toward the reference electrode 10 through the third layer $L_3$. Here, an electric current Is, designated at 18, proportional to the amount of oxygen ions flows between the cathode-side pump electrode 16 and the reference electrode 10.

Figure 2:
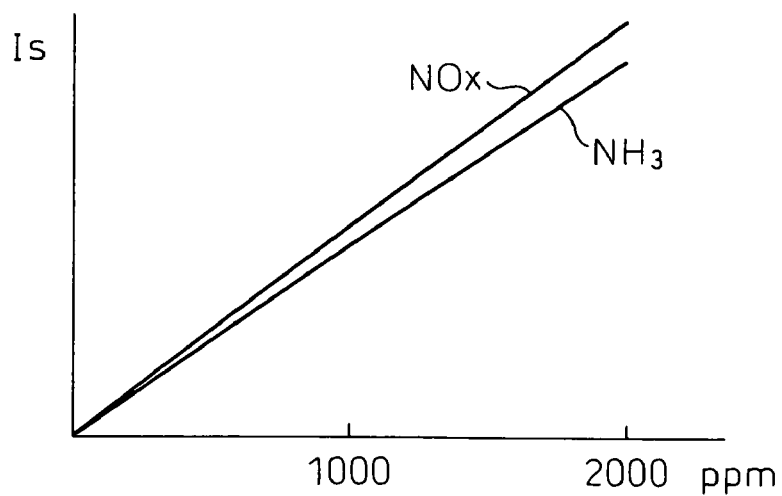
FIG. 2 is a diagram illustrating a relationship among the NOx concentration, ammonia concentration and sensor current Is.

On the other hand, ammonia ($NH_3$) contained in the exhaust gas is decomposed into NO and $H_2O$ ($4NH_3+5O_2 \rightarrow 4NO+6H_2O$) in the first chamber 4, and the decomposed NO flows into the second chamber 5 passing through the second diffusion rate-determining member 3. The NO is decomposed into $N_2$ and $O_2$ on the cathode-side pump electrode 16, and $O_2$ that is formed by decomposition migrates as oxygen ions toward the reference electrode 10 through the third layer $L_3$. In this case, too, the current Is flows in proportion to the $NH_3$ concentration in the exhaust gas. Thus, the $NH_3$ concentration in the exhaust gas is detected from the current Is. FIG. 2 illustrates a relationship between the current Is, the NOx concentration and the $NH_3$ concentration in the exhaust gas. It will be understood from FIG. 2 that the current Is varies in proportion to the NOx concentration and the $NH_3$ concentration in the exhaust gas.

Further, as the oxygen concentration increases in the exhaust gas (i.e., as the air-fuel ratio becomes lean), oxygen is pumped out in increased amounts from the first chamber 4 and the current Ip designated at 19 increases. Therefore, the air-fuel ratio of the exhaust gas is detected from the current Ip.

A heater 20 is arranged between the fifth layer $L_5$ and the sixth layer $L_6$ for heating the sensor portion of the NOx sensor. Due to the electric heater 20, the sensor portion of the NOx sensor is heated at 700 to 800° C.

Next, described below is how to detect (calculate) the NOx concentration in the embodiment. As described above, the current Is designated at 18 assumes a value that varies in proportion to the amount of oxygen ions flowing between the cathode-side pump electrode 16 and the reference electrode 10, the oxygen ions being formed from $O_2$ formed by decomposition of NOx on the cathode-side pump electrode 16. If briefly described, therefore, the current Is assumes a value proportional to the concentration of oxygen formed by decomposition of NOx on the cathode-side pump electrode 16. That is, the current Is varies in proportion to the NOx concentration in the second chamber 5. Therefore, the NOx concentration (or NOx concentration in the exhaust gas) in the second chamber 5 can be learned from the value of current Is.

Strictly speaking, however, oxygen ions flowing between the cathode-side pump electrode 16 and the reference electrode 10 include oxygen ions that are formed by the cathode-side pump electrode 16 from oxygen remaining in the exhaust gas without being pumped out and are flowing between the cathode-side pump electrode 16 and reference electrode 10. Accordingly, the current Is includes a current due to the amount of oxygen ions formed from NOx in the second chamber 5 and a current due to the amount of oxygen ions formed from oxygen that originally exists in the second chamber 5.

Here, as described above, the current Im designated at 14 assumes a value in proportion to the amount of oxygen ions formed upon coming in contact with the second cathode-side pump electrode 12 and are flowing between the second cathode-side pump electrode 12 and the first anode-side pump electrode 8. Therefore, the current Im corresponds to a current due to the amount of oxygen ions formed from oxygen that is existing in the second chamber 5 from the first time.

As described above, the current Is includes a current due to NOx in the second chamber 5 and a current due to originally oxygen existing in the second chamber 5, while the current Im includes a current due to oxygen originally existing in the second chamber 5. As represented by the following formula (1), therefore, a value In obtained by subtracting the current Im from the current Is will assume a value which is proportional to the NOx concentration in the second chamber 5.

$$In = Is - Im \quad (1)$$

More strictly speaking, further, if the means constituted by the cathode-side pump electrode 16 and the reference electrode 10 to produce the current Is, is called a "sensor cell", then, the sensor cell includes an output error inherent therein. According to the first embodiment of the present invention, therefore, the NOx concentration [NOx] is calculated according to the following formula (2), $$[NOx] = (Is - Im) \times K - K_{off} \quad (2)$$

where K is a coefficient for converting, into a NOx concentration, a value Is−Im obtained by subtracting a value Im of current (hereinafter referred to as "monitor current") output from the monitor cell (i.e., means constituted by the second cathode-side pump electrode and the first anode-side pump electrode 8 and for producing a current Im) from a value Is of current (hereinafter referred to as "sensor current") output from the sensor cell, and $K_{off}$ is a coefficient (hereinafter also referred to as "output error correction coefficient") for correcting the output error inherent in the sensor cell.

According to the formula (2), the NOx concentration in the exhaust gas can be correctly calculated (detected) when the coefficients K and $K_{off}$ assume proper values.

The output characteristics of the sensor cell and the output characteristics of the monitor cell may often differ depending upon their sizes and the kinds of the constituent materials. If there is a difference in the output characteristics between the sensor cell and the monitor cell, the value In calculated according to the above formula (2) often may not vary in proportion to the NOx concentration in the exhaust gas.

According to a second embodiment of the invention, therefore, the NOx concentration [NOx] is calculated based on the sensor cell current Is and the monitor cell current Im according to the following formula (3), $$[NOx] = (Is - Im \times K_3 - K_2) \times K_1 \quad (3)$$

where $K_3$ is a coefficient for correcting the output characteristic of the monitor cell so as to be brought into agreement with the output characteristics of the sensor cell, and $K_2$ is a coefficient for bringing the output characteristics of the monitor cell after corrected by $K_3$ into agreement with the output characteristics of the sensor cell. That is, multiplying the monitor cell current Im by the coefficient $K_3$ is not enough to bring the output characteristics of the monitor cell into perfect agreement with the output characteristics of the sensor cell. Therefore, the coefficient $K_2$ is used for correcting a deviation between the output characteristics of the monitor cell and the output characteristics of the sensor cell that cannot be brought into agreement with each other by using the coefficient $K_3$. Further, a coefficient $K_1$ is for converting the value Is−Im×$K_3$−$K_2$ into the NOx concentration [NOx].

According to this formula (3), the NOx concentration in the exhaust gas can be correctly calculated (detected) when the coefficients $K_1$, $K_2$ and $K_3$ assume proper values.

In the above NOx sensor, means constituted by the first cathode-side pump electrode 7 and the first anode-side pump electrode 8 for releasing oxygen from the exhaust gas to the external side is referred to as "pump cell". Namely, the "pump cell" works to release oxygen from the exhaust gas arriving at the NOx sensor to the external side. When the supply of fuel into the combustion chamber of the internal combustion engine is interrupted, the oxygen concentration in the exhaust gas emitted from the combustion chamber and arriving at the NOx sensor increases rapidly to becomes greater than that when the internal combustion engine is normally operating (i.e., becomes greater than that of under the conditions except when no fuel is being supplied into the combustion chamber). More concretely, the oxygen concentration in the exhaust gas arriving at the NOx sensor at this moment becomes nearly equal to the oxygen concentration in the atmosphere. Therefore, to maintain the oxygen concentration in the first chamber 4 at 1 p.p.m. at this time, the voltage of the first pump voltage source 9 (hereinafter referred to as "pump voltage" and "Vp" is attached to it) must be increased rapidly.

As described earlier, however, the pump voltage Vp is controlled by feedback relying upon the voltage $V_0$ designated at 11, and the feedback control includes a predetermined control lag. Therefore, even if the oxygen concentration in the exhaust gas arriving at the NOx sensor increases rapidly, the pump voltage Vp increases only gradually. In this case, the oxygen concentration in the first chamber 4 is not maintained at 1 p.p.m. for a predetermined period of time. Therefore, the NOx concentration finally calculated (detected) based on the output current Is of the sensor cell is deviated from a true value (when no fuel is being fed to the combustion chamber, the NOx concentration is nearly zero in the exhaust gas and, hence, concretely speaking, the true value here stands for "zero").

Figure 3A:
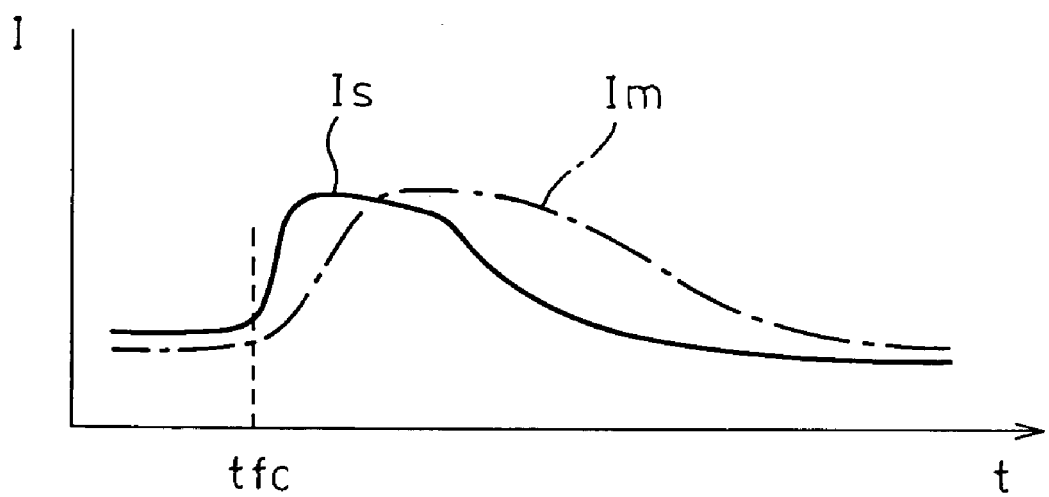
FIG. 3A is a diagram illustrating the shift of sensor current Is and monitor current Im after the start of fuel cutting.
Figure 3B:
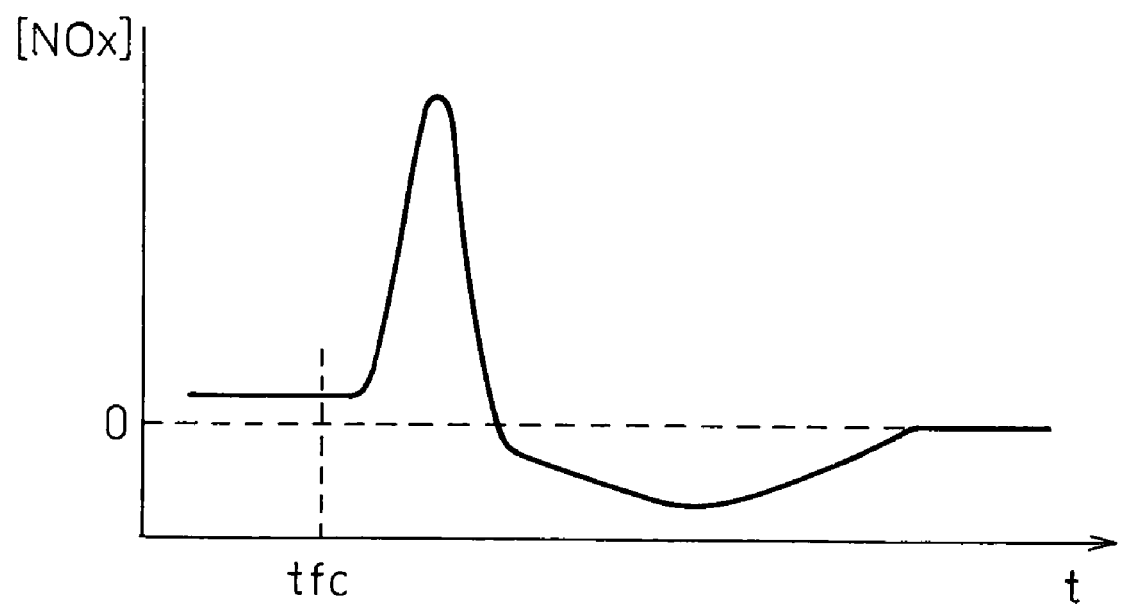
FIG. 3B is a diagram illustrating the shift of NOx concentration [NOx] calculated after the start of fuel cutting.

Namely, in this case, the monitor current Im and the sensor current Is shift with the passage of time as shown in, for example, FIG. 3A, and the NOx concentration [NOx] calculated from the above formula (2) or (3) shifts with the passage of time as shown in FIG. 3B. That is, in an example of FIG. 3A (the abscissa t represents the time, the ordinate I represents the current, a solid line Is represents the shift of sensor current, and a dot-dash chain line Im represents a monitor current), the supply of fuel into the combustion chamber is interrupted at a time $t_{fc}$ (the interruption of fuel supply to the combustion chamber is hereinafter also referred to as "fuel cut", and the state where no fuel is supplied to the combustion chamber is also referred to as "when the fuel is cut"). As the fuel supply to the combustion chamber is interrupted at the time $t_{fc}$, however, the sensor current Is increases rapidly. However, the monitor cell and the sensor cell have their response characteristics, sensitivities and flow of gas around them (due to mounting positions) different from each other and, hence, the monitor current Im does not increase in quite the same manner as the sensor current Is. When the supply of fuel into the combustion chamber is interrupted at the time $t_{fc}$, therefore, the calculated NOx concentration [NOx] increases greatly as illustrated in FIG. 3B (the abscissa t represents the time as in FIG. 3A, the ordinate [NOx] represents the NOx concentration calculated according to the formula (2) or (3), and a solid line represents a shift of the NOx concentration). When the fuel is cut, the NOx concentration in the exhaust gas is nearly zero. Therefore, the NOx concentration [NOx] calculated after the start of fuel cut does not represent a true value.

In the example illustrated in FIG. 3A, further, the monitor current Im increases rapidly after the passage of a predetermined period of time from the start of the fuel cut and remains stable at a large value while the sensor current Is gradually decreases. As illustrated in FIG. 3B, therefore, the calculated NOx concentration [NOx] decreases rapidly to become lower than zero. In this case, too, the calculated NOx concentration [NOx] does not represent a true value. After the passage of relatively long periods of time from the start of the fuel cut, both the sensor current Is and the monitor current Im remain stable at small values, and the NOx concentration [NOx] is calculated to be nearly zero.

As described above, if the NOx concentration is calculated as in the normal state even after the start of the fuel cut, the NOx concentration that is calculated fails to represent a true value. In order to correctly calculate (detect) the NOx concentration in the exhaust gas when the fuel is cut, therefore, it is necessary to carry out a particular control operation for the NOx sensor. In this embodiment, therefore, the following particular control (hereinafter referred to as "control of when the fuel is cut") is effected when the fuel is cut.

That is, when the fuel is cut, an increase of the pump voltage Vp at one time results in an increase in the amount of oxygen pumped out from the exhaust gas by the pump cell, and the oxygen concentration in the first chamber 4 can be lowered rapidly. In the control when the fuel is cut according to the first embodiment of the invention, therefore, the pump voltage Vp is increased rapidly up to a predetermined value (which is capable of lowering the oxygen concentration in the exhaust gas that contains oxygen at a concentration nearly equal to the oxygen concentration in the atmosphere down to 1 p.p.m. rapidly, hereinafter referred to as "predetermined pump voltage" and its setting method will be described later) at the start of the fuel cut. According to this method, even when the fuel is cut, the oxygen concentration in the first chamber 4 is maintained at 1 p.p.m. simultaneously with the cutting (or immediately after the cutting), and the NOx concentration can be correctly calculated (detected). Immediately after the pump voltage Vp is increased up to the predetermined pump voltage (or after the passage of a predetermined period of time), the pump voltage Vp is controlled by feedback relying on the voltage $V_0$ designated at 11 so that the oxygen concentration in the first chamber 4 is maintained at 1 p.p.m.

In the control when the fuel is cut according to a second embodiment of the invention, when it is expected that the fuel cut will start, the pump voltage Vp is increased rapidly to a predetermined value (this value, too, is the same as the above predetermined pump voltage and is similarly referred to as the "predetermined pump voltage"). Therefore, even when the fuel is cut, the oxygen concentration in the first chamber 4 is maintained at 1 p.p.m. simultaneously with the fuel cut (or immediately thereafter), and the NOx concentration can be correctly calculated (detected). Immediately after the pump voltage Vp is increased up to the predetermined pump voltage (or after the passage of a predetermined period of time), the pump voltage Vp is controlled by feedback relying on the voltage $V_0$ designated at 11 so that the oxygen concentration in the first chamber 4 is maintained at 1 p.p.m.

In the above formula (2) as described above, the coefficient $K_{off}$ is for correcting an error due to the output error inherent in the sensor cell. Here, the NOx concentration in the exhaust gas arriving at the NOx sensor when the fuel is cut is zero. In the above formula (2), therefore, there will be obtained $(Is-Im) \times K - K_{off} = 0$ if the coefficient $K_{off}$ assumes a suitable value. In other words, if $(Is-Im) \times K - K_{off}$ assumes a value other than zero, then, this value is a true output error correction coefficient. That is, when the fuel is cut, the value [NOx] output from the NOx sensor according to the above formula (2) is an error due to the output error inherent in the sensor cell.

In this embodiment, therefore, the value [NOx] calculated according to the above formula (2) when the fuel is cut (preferably, when the fuel is cut and a change in the sensor cell current Is lies within a predetermined range (or is, preferably, nearly zero)), is used as a new output error correction coefficient $K_{off}$. Namely, in this embodiment, the output error correction coefficient $K_{off}$ is learned every time when the fuel is cut. This makes it possible to correctly calculate (detect) the NOx concentration.

Here, in this embodiment, the oxygen concentration in the first chamber 4 is maintained at 1 p.p.m. even when the fuel is cut. In other words, the pump voltage Vp at this time assumes a value which makes it possible to maintain the oxygen concentration in the first chamber 4 at 1 p.p.m. when the fuel is cut. Or, in other words, the pump voltage Vp with which the oxygen concentration in the first chamber 4 is maintained at 1 p.p.m. when the fuel is cut corresponds to the above-mentioned predetermined value (i.e., pump voltage that is achieved when the fuel is cut).

In this embodiment, therefore, the pump voltage Vp when the fuel is cut (preferably, when the fuel is cut and a change in the monitor current Im lies within a predetermined range (or is, preferably, nearly zero)), is used as a new predetermined pump voltage. Namely, in this embodiment, the predetermined pump voltage is learned every time when the fuel is cut. This makes it possible to correctly calculate (detect) the NOx concentration.

FIG. 4 is a flowchart of control for calculating (detecting) the NOx concentration according to the invention. In the flowchart of FIG. 4, it is judged, first, at step 10 whether a fuel cut flag $F_{fc}$ is set ($F_{fc}=1$). Here, the fuel cut flag $F_{fc}$ is set when it is judged that the fuel be cut and is reset ($F_{fc}=0$) when it is judged that the fuel cut has ended.

When it is judged at step 10 that $F_{fc}=0$, the routine proceeds to step 17 where the NOx concentration [NOx] is calculated according to the above formula (3). When it is judged at step 10 that $F_{fc}=1$, the routine proceeds to step 11 where the pump voltage Vp is elevated up to the predetermined pump voltage $Vp_{fc}$. Then, at step 12, a signal $S_{fc}$ is transmitted for permitting the execution of fuel cut. Namely, in this example, the fuel is cut after the pump voltage Vp is increased up to the predetermined pump voltage $Vp_{fc}$. The routine, then, proceeds to steps 13 and 15.

At step 13, it is judged whether a change in the sensor current $Is_{n+1}$ of this time from the sensor current Sn of the previous time is within a predetermined range ($|Is_n - Is_{n+1}| < \alpha$). Here, however, it may be so judged whether a change in the sensor current $Is_{n+1}$ of this time from the sensor current $Is_n$ of the previous time is nearly zero ($|Is_n - Is_{n+1}| \approx$ zero). When it is so judged at step 13 that $|Is_n - Is_{n+1}| < \alpha$, the routine proceeds to step 14 to calculate the output error correction coefficient $K_{off}$. Concretely speaking, a value output from the NOx sensor at this time is an output error correction coefficient $K_{off}$. When it is judged at step 13 that $|Is_n - Is_{n+1}| \geq \alpha$, on the other hand, the routine ends.

At step 15, on the other hand, it is judged whether a change in the pump current $Ip_{n+1}$ of this time from the pump current $Ip_n$ of the previous time is within a predetermined range ($|Ip_n - Ip_{n+1}| < \beta$). Here, however, it may be judged whether a change in the pump current $Ip_{n+1}$ of this time from the pump current $Ip_n$ of the previous time is nearly zero ($|Ip_n - Ip_{n+1}| \approx$ zero). When it is judged at step 15 that $|Ip_n - Ip_{n+1}| < \beta$, the routine proceeds to step 16 to calculate the predetermined pump voltage $Vp_{fc}$. Concretely speaking, a pump voltage Vp at this moment is used as the predetermined pump voltage $Vp_{fc}$. When it is judged at step 15 that $|Ip_n - Ip_{n+1}| \geq \beta$, on the other hand, the routine ends.

In the foregoing was described a NOx sensor equipped with three cells, i.e., pump cell, monitor cell and sensor cell according to the embodiment of the invention. The invention, however, can also be applied to the NOx sensor having two cells only, i.e., pump cell and sensor cell.

The present invention can further be applied not only to detecting the NOx concentration but also to calculating (detecting) the ammonia concentration. The invention can be further applied to calculating (detecting) the sulfur oxide (SOx) concentration in the exhaust gas based on the sensor cell current Is. More generally, the present invention can detect the concentration of a particular component based on the amount of oxygen that is formed when the particular component is decomposed.

In the above embodiment, the control operation is executed when the fuel is cut (or when it is expected that the fuel will be cut). Generally, however, the control operation may be executed when the fuel is cut or when the oxygen concentration in the exhaust gas has greatly increased (or when it is expected that the oxygen concentration will greatly increase in the exhaust gas). More generally, therefore, it can be said that the invention executes the control operation when the fuel is cut or when the rate of increase of oxygen concentration in the exhaust gas becomes greater than a predetermined rate (or when it is expected that the rate of increase of the oxygen concentration in the exhaust gas will become greater than a predetermined rate).

It can be said that the operation for increasing the pump voltage Vp up to a predetermined pump voltage $Vp_{fc}$ is the one for increasing the capability for discharging oxygen from the exhaust gas in the NOx sensor. More generally, therefore, it can be said that the invention increases the capability for discharging oxygen from the exhaust gas in the NOx sensor when the fuel is cut.

Figure 5:
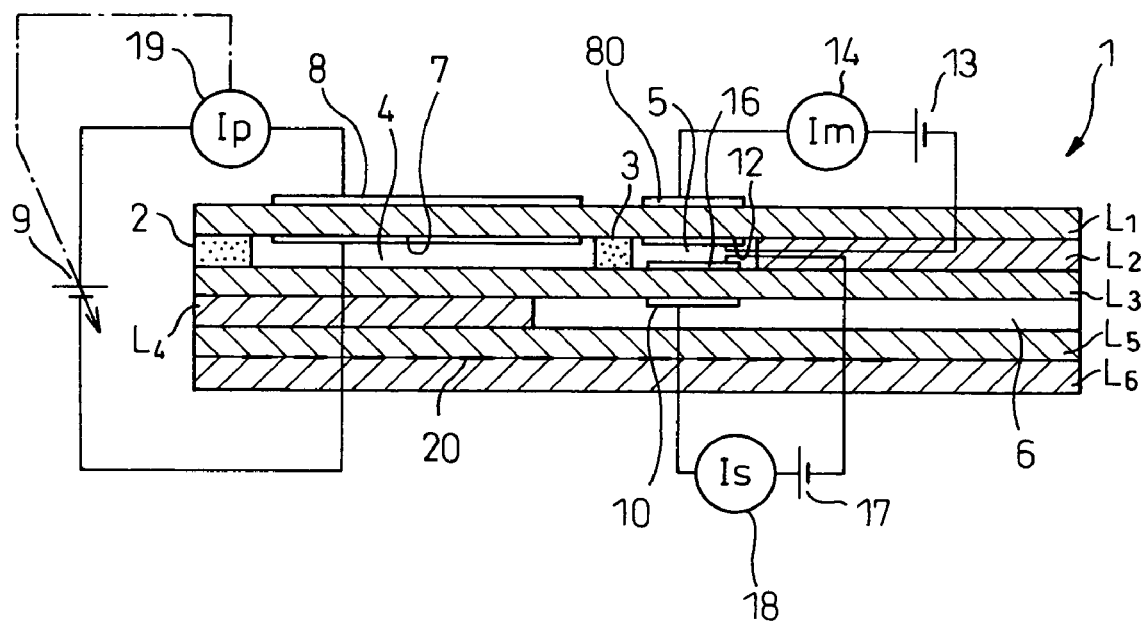
FIG. 5 is a view illustrating a sensor portion of a constitution separate from that of the sensor portion illustrated in FIG. 1.

The invention can similarly be applied even to the NOx sensor having a sensor portion 1 as illustrated in FIG. 5. That is, the sensor portion 1 illustrated in FIG. 5 includes six electrolytic layers $L_1$ to $L_6$ of oxygen ion conducting solid materials laminated one upon the other as in the sensor portion illustrated in FIG. 1. As in the example of FIG. 1, a first diffusion rate-determining member 2 and a second diffusion rate-determining member 3 are arranged between the first layer $L_1$ and the third layer $L_3$ to thereby form a first chamber 4 and a second chamber 5. As in the example of FIG. 1, further, an atmospheric chamber 6 is formed between the third layer $L_3$ and the fifth layer $L_5$. As in the example of FIG. 1, further, a first cathode-side pump electrode 7 is formed on the inner peripheral surface of the first layer $L_1$, a first anode-side pump electrode 8 is formed on the outer peripheral surface of the first layer $L_1$, and a voltage is applied across the electrodes 7 and 8 from the first pump voltage source 9. When the voltage is applied across the electrodes 7 and 8 from the first pump voltage source 9, oxygen in the first chamber 4 is pumped out through the first layer $L_1$ and, at this time, there flows a threshold current Ip, designated at 19, proportional to the amount of oxygen that is pumped out. In the example illustrated in FIG. 5, the voltage of the voltage source 9 is controlled by feedback based on the threshold current Ip.

Further, a second cathode-side pump electrode 12 is formed on the inner peripheral surface of the first layer $L_1$ facing the second chamber 5, a second anode-side pump electrode 80 is formed on the outer peripheral surface of the first layer $L_1$, and a voltage is applied across these electrodes 12 and 80 from a second pump voltage source 13. When the voltage is applied across the electrodes 12 and 80 from the second pump voltage source 13, oxygen in the second chamber 5 is pumped out through the first layer $L_1$ and, at this time, there flows a limiting current Im, designated at 14, proportional to the amount of oxygen that is pumped out. That is, the limiting current Im represents the oxygen concentration in the second chamber 5.

As in the example of FIG. 1, further, an anode-side electrode 10 is formed on the wall surface of the third layer $L_3$ facing the atmospheric chamber 6, a cathode-side pump electrode 16 is formed on the wall surface of the third layer $L_3$ facing the second chamber 5, and a voltage is applied across these electrodes 10 and 16 from a voltage source 17. When the voltage is applied across the electrodes 10 and 16 from the voltage source 17, NOx is decomposed into nitrogen ($N_2$) and oxygen ($O_2$) on the cathode-side pump electrode 16, and oxygen thus formed by decomposition and oxygen existing in the second chamber 5 are pumped out to the external side (atmospheric chamber 6) via the third layer $L_3$. Here, there flows a limiting current Is, designated at 18, which is proportional to the amount of oxygen that is pumped out. Namely, the limiting current Is represents the total concentration of oxygen existing in the second chamber 5 and of oxygen formed by the decomposition of NOx. In the example of FIG. 5, therefore, a value obtained by subtracting the limiting current Im from the limiting current Is represents the NOx concentration in the exhaust gas.

The invention described above offers the following advantages. Namely, in the concentration detector equipped with oxygen-discharging means for discharging oxygen in the gas, if the oxygen-discharging capability of the oxygen-discharging means remains constant without being increased despite the oxygen concentration in the gas being increased rapidly, then, the oxygen concentration remains high in the gas despite oxygen being discharged from the gas by the oxygen-discharging means. Here, if the concentration detector is the one designed to detect the concentration of a particular component based on the amount of oxygen formed when the particular component is decomposed, the concentration of the particular component that is detected does not necessarily represent a true value if the oxygen concentration in the gas remains high after oxygen is discharged by the oxygen-discharging means. According to the present invention, on the other hand, when the rate of increase of the oxygen concentration in the gas is greater than a predetermined rate, the oxygen-discharging capability is increased by the oxygen-discharging means. According to the present invention, therefore, the concentration of the particular component that is detected represents a true value. Namely, the concentration detector normally works when the fuel is cut.

While the invention has been described by reference to specific embodiments chosen for purposes of illustration, it should be apparent that numerous modifications could be made thereto by those skilled in the art, without departing from the basic concept and scope of the invention.

The invention claimed is:

1. A concentration detector for detecting the concentration of a particular component in a gas, which component forms oxygen by decomposition, based upon the amount of oxygen formed by the decomposition of the particular component, comprising:
   an oxygen-forming unit that forms oxygen by decomposing the particular component;

an oxygen-discharging unit that discharges oxygen from the gas before oxygen is formed by the oxygen-forming unit;

an oxygen-discharging capability-increasing unit that increases the oxygen-discharging capability of the oxygen-discharging unit when the rate of increase of the oxygen concentration in the gas is greater than a first predetermined rate before oxygen is formed by the oxygen-forming unit; and an oxygen concentration-maintaining unit that maintains the oxygen concentration of the gas after the oxygen-discharging unit discharges oxygen from the gas.

2. A concentration detector as set forth in claim 1, wherein:

the oxygen-discharging capability-increasing unit increases the oxygen-discharging capability of the oxygen-discharging unit by varying voltage applied to the the oxygen-discharging unit;

the oxygen concentration-maintaining unit maintains the oxygen concentration in the gas by varying voltage applied to the oxygen concentration-maintaining unit; and a degree of increasing the oxygen-discharging capability of the oxygen-discharging unit by the oxygen-discharging capability-increasing unit is determined based on the voltage applied to the oxygen-discharging unit after the oxygen-discharging capability of the oxygen-discharging unit is increased by the oxygen-discharging capability-increasing unit.

3. A concentration detector as set forth in claim 1, wherein the concentration detector is disposed in an exhaust gas passage of an internal combustion engine, wherein when no fuel is supplied to the internal combustion engine, the rate of increase of the oxygen concentration in the gas becomes greater than the predetermined rate before oxygen is formed by the oxygen-forming means.

4. A concentration detector as set forth in claim 1, wherein the particular component is one of nitrogen oxide and ammonia.

5. A concentration detector for detecting the concentration of a particular component in a gas, which component forms oxygen by decomposition, based upon the amount of oxygen formed by the decomposition of the particular component, comprising:

oxygen-forming means for forming oxygen by decomposing said particular component;

oxygen-discharging means for discharging oxygen from the gas before oxygen is formed by the oxygen-forming means;

oxygen-discharging capability-increasing means for increasing the oxygen-discharging capability of the oxygen-discharging means when the rate of increase of the oxygen concentration in the gas is greater than a predetermined rate before oxygen is formed by the oxygen-forming means;

concentration calculation means for calculating the concentration of the particular component in the gas based on a current generated depending upon the oxygen concentration in the gas after oxygen is formed by the oxygen-forming means; and means for calculating a coefficient for correcting a calculation error in the concentration calculation means based on a current generated depending upon the oxygen concentration in the gas when the rate of increase of the oxygen concentration in the gas becomes greater than the predetermined rate before oxygen is formed by the oxygen-forming means.

* * * * *